(12) United States Patent
Sun et al.

(10) Patent No.: US 6,465,709 B1
(45) Date of Patent: Oct. 15, 2002

(54) EXOTHERMIC BANDAGE

(75) Inventors: Ying Sun, Somerville, NJ (US); Ralph W. Oakeson, Racine, WI (US); Stephen J. Wisniewski, Doylestown, PA (US); Jonas C. T. Wang, West Windsor, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 09/611,865

(22) Filed: Jul. 7, 2000

Related U.S. Application Data

(60) Provisional application No. 60/142,878, filed on Jul. 8, 1999.

(51) Int. Cl.[7] .................................................. A61F 13/00
(52) U.S. Cl. ............................. 602/48; 602/41; 602/42; 602/43; 602/44; 602/45; 602/46
(58) Field of Search ...................................... 602/41–48

(56) References Cited

U.S. PATENT DOCUMENTS

| 3,315,665 A | 4/1967 | MacLeod |
| 3,950,158 A | 4/1976 | Gossett |
| 3,964,482 A | 6/1976 | Gerstel et al. |

(List continued on next page.)

FOREIGN PATENT DOCUMENTS

| DE | 195 25 607 A1 | 1/1997 |
| EP | 0 429 842 A2 | 6/1991 |
| GB | 2 303 208 A | 2/1997 |
| WO | PCT 86/07269 A1 | 12/1986 |
| WO | PCT 92/07618 A1 | 5/1992 |
| WO | PCT 93/17754 A1 | 9/1993 |
| WO | PCT 94/23777 A1 | 10/1994 |
| WO | PCT 95/30410 A3 | 11/1995 |
| WO | PCT 96/17648 A1 | 11/1995 |
| WO | PCT 96/00110 A1 | 1/1996 |
| WO | PCT 96/37256 A1 | 11/1996 |
| WO | PCT 97/04832 | 2/1997 |
| WO | PCT 97/12644 A1 | 4/1997 |
| WO | PCT 97/48440 | 12/1997 |
| WO | PCT 97/48441 A1 | 12/1997 |
| WO | PCT 97/48442 | 12/1997 |
| WO | PCT 98/11937 | 3/1998 |
| WO | PCT 98/28037 A1 | 7/1998 |
| WO | PCT 98/28038 A1 | 7/1998 |
| WO | PCT 98/29134 | 7/1998 |
| WO | PCT 98/46124 A1 | 10/1998 |

OTHER PUBLICATIONS

Sun, Y. Skin Absorption Enhancement by Physical Means: Heat, Ultrasound, and Electricity. Transdermal and Topical Drug Delivery Systems. (1997) 327–355.
Buyuktimkin N., Buyuktimkin S. Chemical Means of Transdermal Drug Permeation Enhancement. Transdermal and Topical Drug Delivery Systems. (1997) 357–475.
Sun Y., Liu J.C., Xue H. Important Parameters Affecting Iontophoretic Transdermal Delivery of Insulin. Proceed. Intern. Symp. Control. Rel. Bioact. Mater., 17, Controlled Release Society, Inc. (1990) 202–203.
Roberts M. Lai P., Cross S., Yoshida N. Solute Structure as a Determinant of Iontophoretic Transport. Mechanisms of Transdermal Drug Delivery. (1997) 291–349.
Johnson & Johnson Consumer Companies, Inc., U.S. application No. 09/548,771, pending.

(List continued on next page.)

*Primary Examiner*—Michael A. Brown
*Assistant Examiner*—Lalita N. Hamilton
(74) *Attorney, Agent, or Firm*—William E. McGowan

(57) ABSTRACT

The present invention relates to a multi-layer exothermic bandage comprising an oxygen-impermeable layer, a water-impermeable layer, a heating element layer comprising an oxidizable material, and an active agent layer; and the use thereof.

17 Claims, 4 Drawing Sheets

U.S. PATENT DOCUMENTS

| | | |
|---|---|---|
| 4,230,105 A | 10/1980 | Harwood |
| 4,406,658 A | 9/1983 | Lattin et al. |
| 4,655,766 A | 4/1987 | Theeuwes et al. |
| 4,685,911 A | 8/1987 | Konno et al. |
| 4,767,402 A | 8/1988 | Kost et al. |
| 4,790,824 A | 12/1988 | Morrow et al. |
| 4,963,360 A | 10/1990 | Argaud |
| 4,994,267 A | 2/1991 | Sablotsky |
| 5,013,293 A | 5/1991 | Sibalis |
| 5,036,861 A | 8/1991 | Sembrowich et al. |
| 5,042,975 A | 8/1991 | Chien et al. |
| 5,135,478 A | 8/1992 | Sibalis |
| 5,156,591 A | 10/1992 | Gross et al. |
| 5,213,568 A | 5/1993 | Lattin et al. |
| 5,224,927 A | 7/1993 | Tapper |
| 5,250,023 A | 10/1993 | Lee et al. |
| 5,279,543 A | 1/1994 | Gilkfeld et al. |
| 5,279,544 A | 1/1994 | Gross et al. |
| 5,320,607 A | 6/1994 | Ishibashi |
| 5,362,307 A | 11/1994 | Guy et al. |
| 5,386,837 A | 2/1995 | Sterzer |
| 5,399,163 A | 3/1995 | Peterson et al. |
| 5,438,984 A | 8/1995 | Schoendorfer |
| 5,441,490 A | 8/1995 | Svedman |
| 5,527,288 A | 6/1996 | Gross et al. |
| 5,533,971 A | 7/1996 | Phipps |
| 5,540,669 A | 7/1996 | Sage, Jr. et al. |
| 5,582,586 A | 12/1996 | Tachibana et al. |
| 5,591,124 A | 1/1997 | Phipps |
| 5,614,502 A | 3/1997 | Flotte et al. |
| 5,636,632 A | 6/1997 | Bommannan et al. |
| 5,658,583 A * | 8/1997 | Zhang ..................... 424/402 |
| 5,658,892 A | 8/1997 | Flotte et al. |
| 5,662,624 A * | 9/1997 | Sundstrom et al. ......... 604/291 |
| 5,667,491 A | 9/1997 | Pliquett et al. |
| 5,718,955 A | 2/1998 | McGuire et al. |
| 5,853,383 A | 12/1998 | Murdock |
| 5,857,992 A | 1/1999 | Haak et al. |
| 5,885,211 A | 3/1999 | Eppstein et al. |
| 6,050,988 A | 4/2000 | Zuck |
| 6,083,196 A | 7/2000 | Trautman et al. |
| 6,104,952 A | 8/2000 | Tu et al. |

OTHER PUBLICATIONS

Johnson & Johnson Consumer Companies, Inc., U.S. application No. 09/549,147, pending.

Johnson & Johnson Consumer Companies, Inc., U.S. application No. 09/385,284, pending.

Johnson & Johnson Consumer Companies, Inc., U.S. application No. 09/612,357, pending.

Johnson & Johnson Consumer Companies, Inc., U.S. application No. 09/611,865, pending.

Johnson & Johnson Consumer Companies, Inc., U.S. application No. 09/644,093, pending.

* cited by examiner

EXOTHERMIC BANDAGE

This application claims benefit to Provisional Application Ser. No. 60/142,878, Filed Jul. 8, 1999.

FIELD OF THE INVENTION

The present invention relates to a delivery device comprising a heating element and the use thereof for enhanced topical and transdermal delivery of active agents.

BACKGROUND OF THE INVENTION

Topical dosage forms have been widely prescribed for decades in the treatment of systemic diseases and local conditions such as those involved with the skin and underlying tissues. Certain drugs are relatively easy to be delivered via the transdermal or transmucosal route because they can easily permeate through the skin or mucosal membrane at a high potency. Permeation of the drug across the skin or mucosal membrane from a transdermal patch or a mucosal patch is a result of the chemical potential gradient across the skin or mucosal membrane. Examples of these drugs include nitroglycerin, scopolamine, nicotine, hydrocortisone, betamethasone, benzocaine, and lidocaine.

Most drugs and biological active ingredients, however, cannot readily penetrate through the skin or mucosal membrane. Therefore, to increase skin permeation of these drugs, various chemical and physical permeation enhancing methods have been employed. Chemical permeation enhancing agents may be applied typically to increase transdermal delivery of drugs. Generally, chemical permeation enhancing agents are cost effective and safe. An extensive review of chemical penetration enhancing agents is reported in Buyuktimkin et al., "Chemical Means of Transdermal Drug Permeation Enhancement", *Transdermal and Topical Drug Delivery Systems*, Interpharm Press, Inc., 1997, pages 357–475. One major disadvange associated with chemical penetatration enhancers is potential skin irriation.

Physical penetration enhancing methods can also be used to improve transdermal drug delivery. The energy forms employed for this purpose include electricity (e.g., iontophoresis), ultrasound (e.g., phonophoresis) and thermal energy (e.g., heat-assisted delivery), which are reviewed by Sun, "Skin Absorption Enhancement by Physical Means: Heat, Ultrasound, and Electricity", *Transdermal and Topical Drug Delivery Systems*, Interpharm Press, Inc., 1997, pages 327–355.

U.S. Pat. No. 4,898,592 relates to a device for the application of heated transdermally absorbable active substances that includes a carrier impregnated with the transdermally absorbable active substance and a support. The support is a laminate made up of one or more polymeric layers and optionally includes a heat conductive element. This heat conductive element is used for distribution of the patient's body heat such that absorption of the active substance is enhanced. This device, however, has no heat-generating element or function. The use of only a heat conductive element to distribute body heat, however, is not an efficient or reliable method of enhancing transdermal absorption by heating since the amount of body heat given off by a patient can vary depending on the ambient air temperature and the physical conditions of the patient.

U.S. Pat. No. 4,747,841 discloses a method and apparatus for "moxibustion" using a heat-generating element to heat and vaporize "moxall" for treatment of a patient's skin without leaving burn scars. The objective of this method and apparatus, however, is to achieve heat stimulation of the body and not to increase skin permeability.

U.S. Pat. No. 4,230,105 discloses a bandage with a drug and a heat-generating substance, preferably intermixed, to enhance the rate of absorption of the drug by the user's skin. Separate drug and heatgenerating substance layers are also disclosed. Water must be applied to the bandage to activate the heating substance to release solvation heat. Because the exothermal reaction during the hydration of the electrolytes disclosed in this patent only produces a transient low level of heat, it cannot be effectively used as a penetration enhancing method over a long period of time (e.g., for up to one day). Further, the speed of the hydration process is rather difficult to control.

U.S. Pat. No. 4,685,911 discloses a skin patch including a drug component and an optional heating element for melting the drug-containing formulation if the user's body temperature is inadequate to do so. The heating element is not substantially co-extensive with the drug reservoir, the latter being quite thick and, thus, not susceptible to even and rapid onset of heating. There is also no description on how to control the exothermic reaction to have prolonged and even heating.

U.S. Pat. No. 4,963,360 describes an exothermic device having a carrier layer, which comprises a medicinal component, and an exothermic layer, which develops heat when exposed to the air to enhance absorption of the medicinal component through the skin. The exothermic layer comprises a mixture of iron powder, carbon powder, salts (i.e., sodium chloride and aluminum chloride), and water. There is a base sheet to separate the exothermic layer from the medicinal layer in two separate chambers, and an air-permeable film that covers the exothermic layer.

U.S. Pat. No. 5,658,583 describes a heat-generating apparatus for improved dermal permeation of pharmaceuticals. The apparatus includes a thin drug formulation reservoir and a heat-generating chamber separated by a non-permeable wall. The drug formulation reservoir houses a predetermined amount of a formulation containing pharmaceutical agents. The heat-generating/temperature-regulating chamber includes a heat-generating medium consisting of carbon, iron, water and/or salt which is activated upon contact with oxygen in the air. The structure of the apparatus also includes a cover that is not permeable to air, but is perforated with holes to regulate the contact between the heatgenerating medium and air, thereby, controlling the heating temperature.

U.S. Pat. No. 5,662,624 describes a heat dressing for treatment of skin areas comprising a heat generating unit and a liquid-absorbing adhesive layer that, prior to use, is coated with a release layer. The adhesive layer is preferably made of a hydro-colloidal material and may optionally contain one or more medicaments or may be coated with alginate fiber mats. The heatgenerating unit generates heat preferably by means of galvanic or chemical energy, and the heat dressing may further comprise elements for controlling the heat development and/or the surface temperature. Such elements include a cover sheet for the heat-generating unit that is perforated for air passage, is covered by a heat-reflecting foil, or is a polymeric foam to better retain the heat.

The present invention relates to an exothermic delivery bandage device for administration of active agents through a barrier membrane (e.g., the skin, nail or mucosal membrane of a human). The advantages of the present device include: significantly simplifying the fabrication process of the device manufacturing; providing a means for the skin under the device to breath; and improving the delivery profile of active agents by minimizing the lag-time in drug delivery to further shorten the onset time for the active agent's intended therapeutic effect.

SUMMARY OF THE INVENTION

In one aspect, the invention features a multi-layer exothermic bandage, said bandage comprising: (a) an oxygen-impermeable layer; (b) a water-impermeable layer; (c) a heating element layer, said heating element layer comprising an oxidizable material, and where said heating element layer is between said oxygen-impermeable layer and said water-impermeable layer; and (d) an active agent layer, said active agent layer comprising an active agent; wherein said water-impermeable layer is between said heating element and said active agent layer.

In another aspect, the invention features a method of topically delivering an active agent to a mammal, said method comprising attaching the bandage of the present invention to a barrier membrane of said mammal.

Other features and advantages of the present invention will be apparent from the detailed description of the invention and from the claims

DETAILED DESCRIPTION OF THE INVENTION

Figure 1:
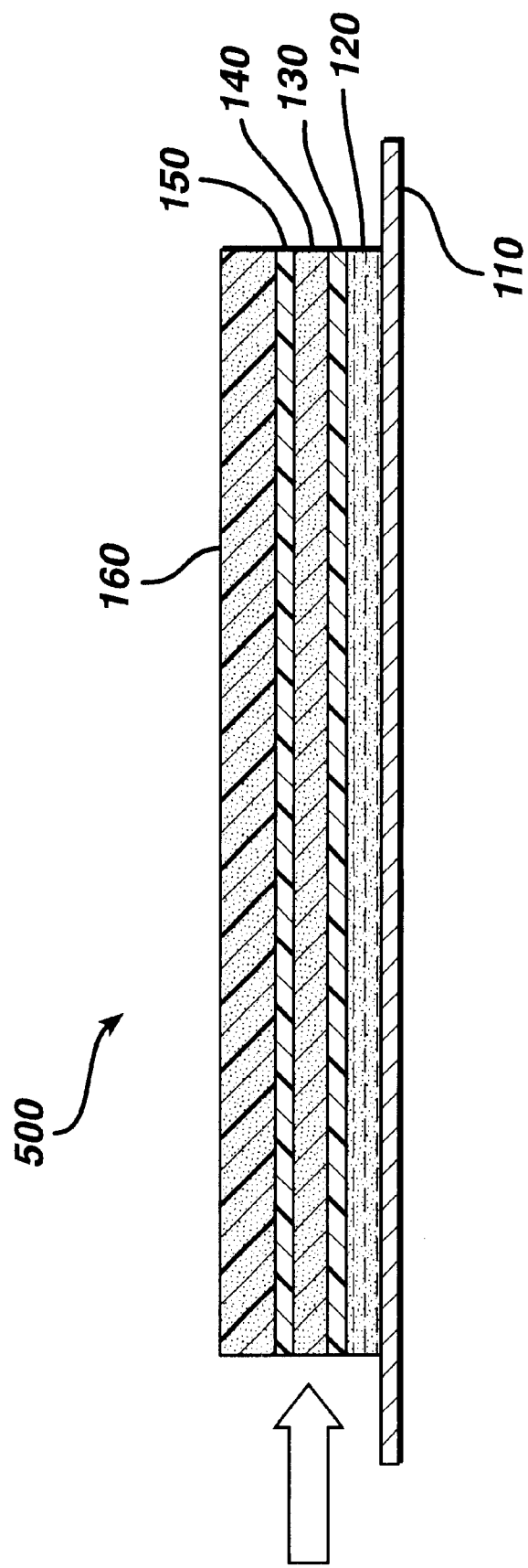
FIG. 1 is a cross-sectional view of an exothermic delivery device for active agents showing one embodiment of the present invention. During operation, oxygen from air reaches the heat-generating layer 140 only from the sides of the device as indicated by the block arrow.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, apatent applications, patents, and other references mentioned herein are incorporated by reference.

The present invention relates to a novel exothermic delivery device of active agent(s) to the barrier membrane, such as human skin, mucosal membrane (e.g., buccal membrane), and nail. The exothermic delivery device of the present invention does not suffer from many of the disadvantages of the existing apparatuses previously described. For example, all of the prior heat-assisted delivery devices based on oxidation heat generation rely on the use of a cavity-like structure or a "chamber" to hold the heat-generating medium. Unfortunately, the chamber design represents a problem for high speed, automated manufacturing process, that is common in bandage manufacturing processes. The exothermic bandage device in the present invention has a multi-laminate structure that can be cut to any size and shape and used as a bandage, thus significantly simplifying the manufacturing process. In addition, prior devices discussed above deprived the skin from gas and moisture exchanging with the environment ("breathing") which is known to cause occlusion-related irritation and therefore, is generally poorly accepted by users.

There, thus, is a need in topical and transdermal delivery of active agents to reduce or to eliminate the therapeutic lag-time for active agents, which is the time required to build up the active agent concentration to the minimum effective level. This problem has not been addressed adequately in the prior devices. Since the skin opermeation of a drug is proportional to the temperature of a drug formulation on the skin (see, e.g., Sun, "Skin Absorption Enhancement by Physical Means: Heat, Ultrasound, and Electricity", *Transdermal and Topical Drug Delivery Systems* (Interpharm Press, Inc., 1997) pages 327–355), it is intuitive that simply increasing the operating temperature of a heat-generating drug delivery device would increase drug delivery and shorten the onset time of the therapeutic effect. However, it is also known that although people can generally tolerate relatively high temperature for a short time (e.g., up to 90° C. in low humility sauna or between 45° C.–50° C. in a hot shower), a prolonged skin contact to a heated body at temperatures above 43° C. could cause serious burn injury.

At the beginning of the application, the exothermic bandage device of the present invention produces more heat to raise the device temperature between about 43° C.–50° C. for a short period of time, since the oxygen from air readily react with the exposed heat-generating layer around the sides of the device. After the initial stage of the oxidation reaction, heat generation is reduced since the exposed reactive material has been consumed and oxygen needs to travel a greater distance to reach deeper temperature of the device is subsequently lowered to between about 40° C.–42° C.

One embodiment of the present invention is represented schematically in FIG. 1. The device 500 of a multi-laminate construction consists of a removable release liner 110, an active-agent containing layer 120, an water-impermeable layer 130 separating the active agent-containing layer 120 of the device from a heat-generating layer 140, an oxygen-impermeable membrane 150, and a heat-insulating layer 160.

The water-impermeable layer 130 is impermeable to the active agent in the active agent-containing layer 120 and any solid or liquid material in the heat-generating layer 140. The water-impermeable layer may be made of flexible material well-known in the art to be impermeable to water, e.g., polymers such as polyethylene, polypropylene, polyvinyl acetate, polyurethane, silicone rubber, and polyvinyl chloride.

The active agent-containing layer 120 comprises the active agent. The active agent-containing layer may further comprise a carrier such as a hydrogel, a polymeric adhesive, a semi-solid carrier such as a cream, lotion, ointment, or liquid crystal. It may also comprise a solid supporting matrix (e.g., a gauze or non-woven or sponge-like materials).

Active agents such as drugs and nutrients and other biologically active agents are incorporated into carrier within the active agent-containing layer 120, e.g., as dissolved molecules and ions, dispersed solid particles, or liquid droplets.

As used herein, the term "active agents" refers drugs and nutrients for local treatment or systemic treatment (e.g., a therapeutic or cosmetic benefit). Typically these agent include, but are not limited to, antihypertensive drugs (e.g., clonidine), analgesic drugs (e.g. fentanyl, ibuprofen, benzocaine, and lidocaine), drugs to assist wound healing (e.g., PDGF), drugs to treat coronary artery diseases (e.g., nitroglycerin, low molecular weight heparin), antimicrobial agents, antipsoriatic agents, antiinflammatory agents, anticancer agents, endocrine and metabolic medication (e.g., testosterone, estradiol), neurologic medications, medication for cessation of chemical additions (e.g., nicotine), motion sickness (scopolamine), and protein and peptide drugs. Most of these agents are known and may be used at concentrations and for durations of time which have proved effective against their respective disease states. These therapeutic agents are described in "Goodman & Gilman's The Pharmcological Basis of Therapeutics", $9^{th}$ Edition by J. G. Hardman, et al., (McGraw-Hill Companies, 1996).

Other active agents include those commonly used as for topical treatment and in cosmetic treatment of skin tissues, such as salicylic acid, benzoyl peroxide, resorcinol, resorcinol monoacetate, and sulfur for acne, topical antibiotics for wounds, topical antifungal drugs to treat fungal infections of the skin and nails, and antipsoriatic drugs to treat psoriatic lesions of the skin and psoriatic nails. Examples of antifungal drugs include but are not limited to miconazole, econazole, ketoconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts. In one embodiement, the antifungal drugs are an azole, an allylamine, or a mixture thereof.

Examples of antibiotics (or antiseptics) include but are not limited to mupirocin, neomycin sulfate bacitracin, polymyxin B, 1-ofloxacin, tetracyclines (chlortetracycline hydrochloride, oxytetracycline hydrochloride and tetrachcycline hydrochoride), clindamycin phsphate, gentamicin sulfate, benzalkonium chloride, benzethonium chloride, hexylresorcinol, methylbenzethonium chloride, phenol, quaternary ammonium compounds, triclocarbon, triclosan, tea tree oil, and their pharmaceutically acceptable salts.

Examples of antipsoriatic drugs include but are not limited to corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone verlerate, hydrocortisone butyrate, aclometasone dipropionte, flurandrenolide, mometasone furoate, methylprednisolone acetate), methotrexate, cyclosporine, calcipotriene and anthraline.

Additional examples of active agents include but are not limited to minoxidil, minoxidil sulfate, retinoids, cysteine and acetyl cysteine, methionine, glutathione, biotin, finasteride and ethocyn, as well as pharmaceutically acceptable salts of these compounds.

The active agents in the present invention may provide certain benefits to the superficial tissues such as the skin, for example: anti-aging, wrinkle removal, depigmentation (e.g., removal of "age spot"), skin tone improvement. The exothermic device in the present invention may be made into facial and body masks of various shape and size to fit the contours of the anatomic locations. The materials for the each layer of the multi-laminate device is preferably pliant for this purpose. The examples of active agents for aforementioned purposes include, but are not limited to: amino acids, and their derivatives, biotin, vitamins, vitamin B complex: thiamine, nicotinic acid, biotin, pantothenic acid, choline riboflavin, vitamin $B_6$, vitamin $B_{12}$, pyridoxine, inositol, carnitine; ascorbic acid, ascorbyl palmitate, vitamin A, vitamin K, vitamin E, vitamin D, cysteine and N-acetyl cysteine, herbal extracts, and their derivatives; soy extracts, calcium pantothenate, calcium carbonate, and calcium gluconate.

Examples of retinoids include but not limited to retinol (Vitamin A alcohol), retinal (Vitamin A aldehyde), retinyl acetate, etinyl palmitate, retinoic cid, 9-cis-retinoic acid and 13-cis-retinoic acid. Examples of flavonoids include but not limited to naringenin, quercetin, catechins (e.g., epigallocatechin gallate), theaflavins, robustaflavone, hinokiflavone, amentoflavone, agathisflavone, volkensiflavone, morelloflavone, rhusflavanone, and succedangeaflavanone.

The exothermic device 500 is suitable to be used deliver agents to remove corn, callus, ingrown toe nails, and diseased nails from infections. The active agents for such a treatment include, but are not limited to, salicylic acid, urea, sodium sulfide, tannic acid, salts of thioglycolic acid, cysteine and acetyl cysteine.

The exothermic device is also suitable to be used deliver agents such as salicylic acid and benzoyl peroxide to treat acne.

The exothermic device is also suitable to be used deliver agents such as retinoids and herbal and soy extracts to provide anti-aging benefits including wrinkle and age-spot removal and improving skin tone.

In another embodiment, the device does not comprise an active agent-containing layer (e.g., it is used to help promote wound healing as a bandage).

The heating unit of the device 500 comprises a heat-generating layer 140 in which heat-generating materials are immobilized. The heat-generating layer 140 comprises a mixture of oxidizable materials (e.g., oxidizable metal powder(s)) and carbon or activated carbon powder. Examples of oxidizable metal powders include, are but not limited to, iron, aluminum, magnesium, zinc, and a mixture thereof. Other oxidizing material that can be used in the present invention to generate heat include those described in U.S. Pat. No. 4,114,591 (e.g., ferrosoferric oxide, plumboblumbic oxide, trimanganese tetroxide, black copper oxide and manganese dioxide in the form of fine particle).

The heat-generating layer also contain electrolytes/salts. The electrolytes/salts include, but are not limited to the salts of sodium, potassium, lithium, calcium, iron, magnesium, and aluminum.

Examples of electrolytes include, but are not limited to, NaCl, KCl, LiCl, $CaCl_2$, $FeCl_3$, $FeCl_2$, $MgCl_2$, $AlCl_3$, $Na_2SO_4$, $K_2SO_4$, $Fe(SO_4)_3$, $FeSO_4$, or $MgSO_4$.

The oxidation material may be immobilized by various means including but not limited to a water-permeable bag, mesh, non-woven pad or other fabric materials, and binding agents (e.g., polymers) such as cellulose polymers, polyacrylic polymers, polyurethanes, gelatins and gums. Exampels of such polymers include hydroxymethylcellulose, hydroxyethylcellulose, hydroxypropylcellulose, cellulose actates, polyvinylvinylidone (PVP), and copolymers of polyacrylic acid and polyacrylates (Carboset®, Carbopol® and Carbomer®).

Water may also be contained in the heat-generating layer 140. In one embodiment, water is added to the heat-generating layer 140 in an oxygen-free environment immediately before being sealed into an oxygen-proof package. In another embodiment, water is absent in the heat-generating layer 140, and the user can add the water to the device 500 at the time of application by wetting it.

There may be optional organic solvents such as glycerin, propylene glycol, and polyethylene glycols of various molecular weights in the heat-generating layer 140. The presence of the binding agent(s), immobilizing structures (e.g., mesh and nonwoven pads), and solvents (water and the organic solvents) further enables the heat-generating layer 140 to maintain its physical integrity both during manufacturing process and during application on the user's skin.

Because the oxygen-impermeable membrane 150 is impermeable to oxygen, oxygen can only reach the heat-generating materials of the heat-generating layer 140 from the side as shown in FIG. 1. The dense, preferably gelled, structure of the heat-generating layer 140 serves as means of controlling the oxygen availability to the oxidizable materials in the heat-generating layer 140, thus leading to prolonged heating. The oxygen-impermeable layer may be made of flexible material well-known in the art to be impermeable to oxygen, e.g., polymers such as polyethylene, polypropylene, polyvinyl acetate, polyurethane, silicone rubber, and polyvinyl chloride.

The heat-insulating layer 160 is a layer with good heat insulation property, preferably being a polymeric foam (e.g., polethylene and polyurethane foam) of sufficient thickness to maintain the generated heat within the device.

All the layers in the multi-laminated device 500 may be held together by adhesives (not shown in the figures) or by heat fusion processes.

Figure 2:
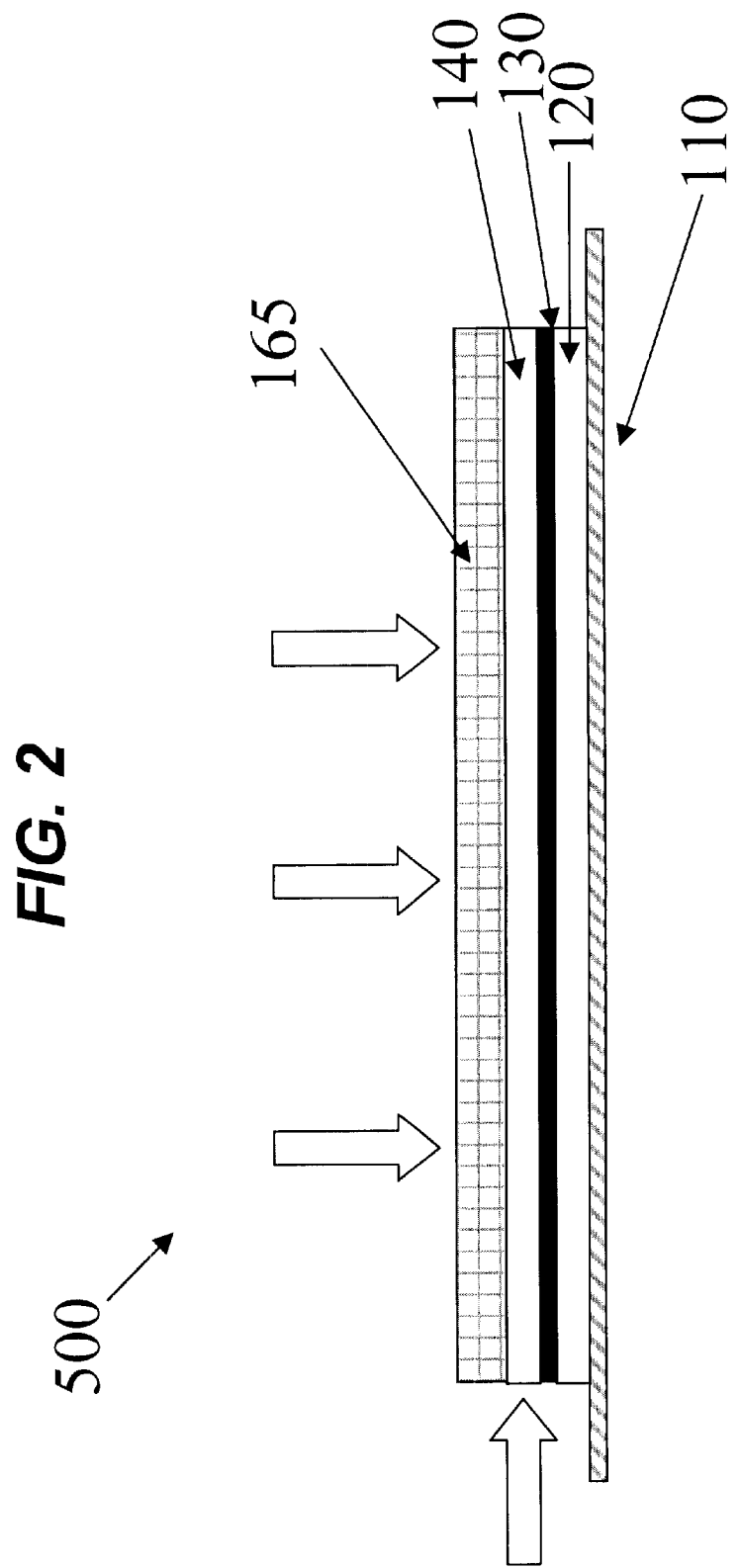
FIG. 2 is a cross-sectional view of an exothermic delivery device for active agents showing one embodiment of the present invention. During operation, oxygen from air reaches the heat-generating layer 140 from the sides of the device and the gas-permeable outer cover 165 as indicated by the block arrows.

Another embodiment of the present invention is schematically represented in FIG. 2. The absence of the oxygen-impermeable membrane 150 enables oxygen to enter the device 500 from the outer cover 165 as shown by the block arrows in FIG. 2. As oxygen can more easily access all of the surface of heat-generating layer 140, this design is more suitable for an exothermic bandage device of a shorter duration.

The outer layer 165 may be made of highly oxygen-permeable polymer membranes such as silicone, polyurethane, polyethylene, and polypropylene. It preferably of a microporous nature such as an open-cell foam, close-cell foam, or open-cell foam with a thin liquid-impermeable polymer layer on one or both side of the outer layer 165. The extent of oxygen permeability of the outer layer 165 is determined by the material it is made of, its thickness, and its porosity. Optional, there may be a removable cover sheet that is essential impermeable to oxygen (not shown in the figures) that is made of similar material as oxygen-impermeable layer 150. The removable cover sheet may be partially or fully removed to adjust the area available to oxygen permeation, thus adjusting the heating produced by the device. The removable cover sheet may have an adhesive coated on one side in order to affix it to the outer layer 165.

During use, the removable cover sheet may be used to completely cover the outer layer to close the oxygen pathway and, thus, stop the heating process. It may later be reopen to re-start the heating process. In this way, the device in the present invention can provide a pulsatile mode of enhance active agent delivery (e.g., alternating between baseline and heat-assisted delivery).

Figure 3A:
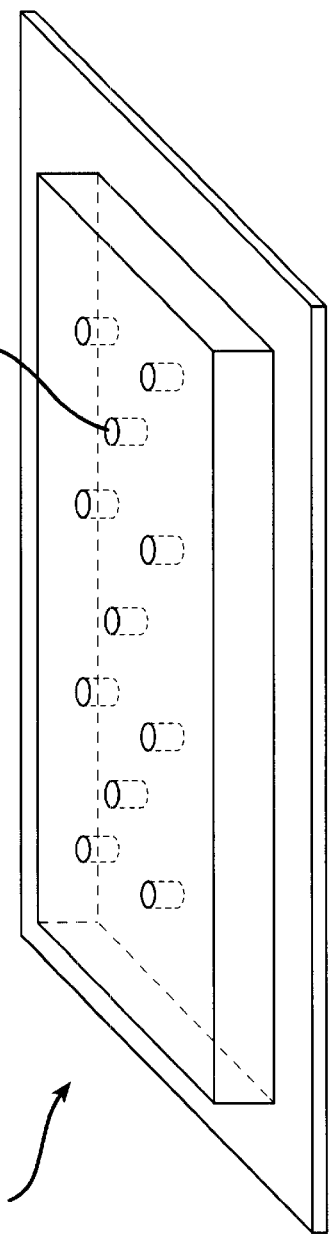
FIG. 3a is a prospective view of an exothermic delivery device with skin-breathing holes showing one embodiment of the present invention.
Figure 3B:
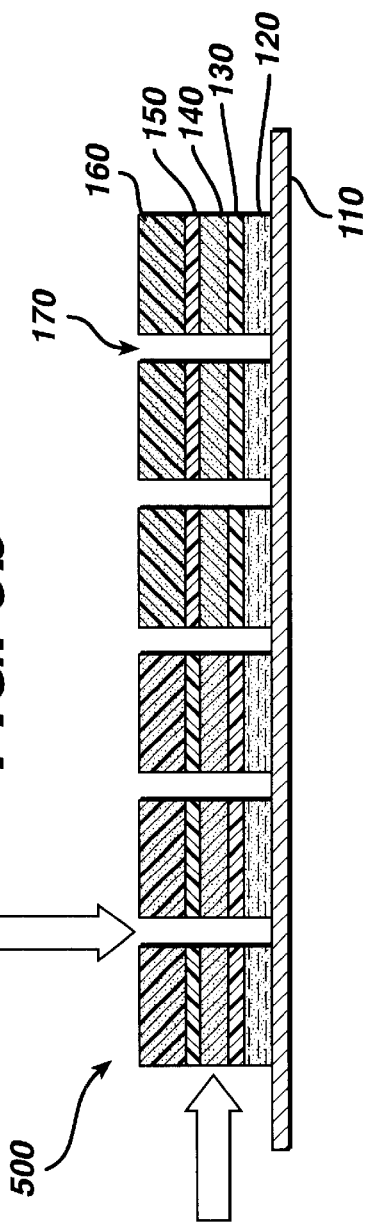
FIG. 3b is a cross-sectional view of the same device showing one embodiment of the present invention. During operation, oxygen from air reaches the heat-generating layer 140 both from the sides of the device and from the "breathable" holes as indicated by the block arrows.

Another embodiment of the present invention is schematically represented in FIGS. 3a & 3b. The exothermic device 500 is perforated with holes to allow the barrier membrane (e.g., the skin) to "breath" during application. There is no limitation on the size, shape and density (i.e., the number of the holes on a given area) of the skin-breathing holes. The skin-breathing holes may optionally go through the removable release liner 110 for the convenience of manufacturing. The skin-breathing holes also serve a way of facilitating oxygen availability to the heat-generating layer 140 and therefore, can be used to adjust the extent and duration of the heating process by their size, shape, density and spacing. Optionally, the skinbreathing holes may also be present on the device shown in FIG. 2.

Figure 4:
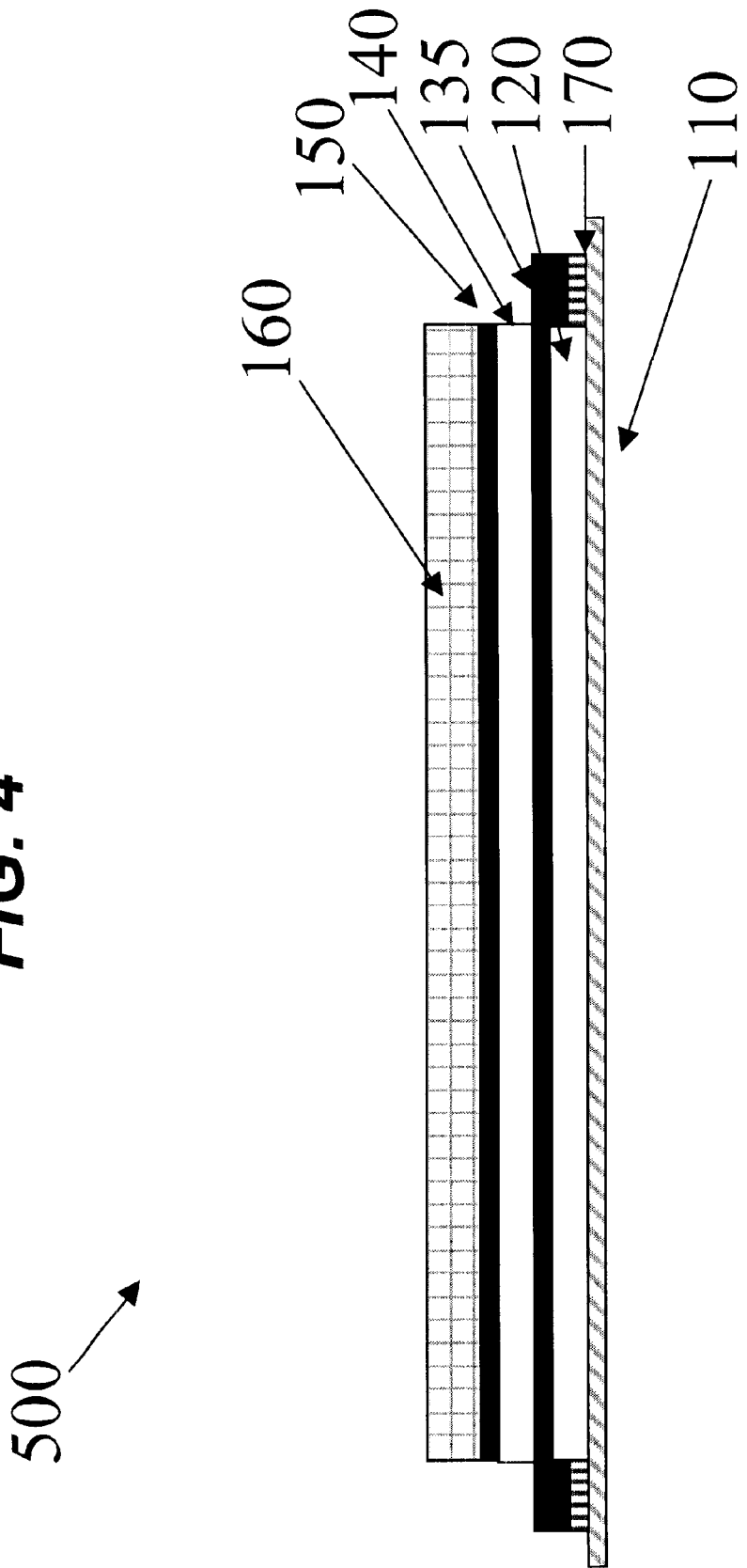
FIG. 4 is a cross-sectional view of an exothermic delivery device for active agents showing one embodiment of the present invention.

Another embodiment of the present invention is schematically represented in FIG. 4. The active agent-containing layer 120 is placed in water-impermeable chamber 135. According to this embodiment, the part of device 500 containing both the active-agent containing layer 120 and the water-impermeable chamber 135 may be a transdermal patch such as one of those transdermal active agent delivery devices and topical treatment devices currently in the market. The examples include transdermal patches of fentanyl (Duragesic® by Janssen Pharmaceutical), nitroglycerin (Nitrodisc® by Roberts Pharmaceutical/G.D., Searle, Nitro-Dur® by Schering/Key Pharmaceutical, and Transderm-Nitro® by Ciba-Geneva, Minitran® by 3M Riker), 17-β-estradiol (Estraderm® by Ciba-Geneva), clonidine (Catapres®-TTS by Boehringer Ingelheim), testosterone (Testoderm® by Alza, Androderm® by SmithKline Beecham), scopolamine (Transderm-Scop® by Ciba-Geigy), nicotine (Nicoderm® by Marion Merrell Dow, Habitrol® by Ciba-Geigy, Nicotrol® by McNeil Consumer Products, Prostep® by Lerderle Lab), and antibiotics, e.g., polymyxin B sulfate and bacitracin zinc (Antibiotic Band-aid® by Johnson & Johnson Consumer Products).

Alternatively, the part of device 500 containing both the active-agent containing layer 120 and the water-impermeable chamber 135 may be a iontophoretic, electroporetic, or phonophoretic device such as one of those devices well-known in the art, e.g., as disclosed in U.S. Pat. Nos. 4,927,408, 5,042,975, 5,224,927, 5,344,394, 5,667,491, 4,767,402, and 5,636,632.

The device 500 may comprise a pressure-sensitive adhesive either within the active agent-containing layer 120 or attached to chamber 135 (see adhesive layer 180 in FIG. 4) to assist affixing the device 500 to the user's barrier membrane (e.g., dermal or mucosal barrier membrane). The adhesive may be a polymeric, pressure sensitive and non-conductive and remains adherent even after prolonged exposure to water. Typically, the adhesive has a broad working temperature range. Suitable adhesive materials include, but are not limited to, silicones, polyisobutylenes and derivatives thereof, acrylics, natural rubbers, and combinations thereof. Suitable silicone adhesives include, but are not limited to, Dow Corningo® 355 available from Dow Corning of Midland, Mich.; Dow Corningo® X7-2920; Dow Corning® X7-2960; GE 6574 available from General Electric Company of Waterford, N.Y.; and silicone pressure sensitive adhesives, such as those disclosed in U.S. Pat. Nos. 2,857,356, 4,039,707, 4,655,767, 4,898,920, 4,925,671, 5,147,916, 5,162,410, and 5,232,702. Suitable acrylic adhesives include, but are not limited to, vinyl acetate-acrylate multipolymers, including, such as Gelvao® 7371, available from Monsanto Company of St. Louis, Mo.; Gelva® 7881; Gelvao® 2943; I-780 medical grade adhesive available from Avery Dennison of Painesville, Ohio; and acrylic pressure sensitive adhesives, such as those disclosed in U.S. Pat. Nos. 4,994,267, 5,186,938, 5,573,778, 5,252,334, and 5,780,050.

A removable liner sheet 110 covers the active agent-containing layer 120 and is attached to the adhesive layer 180 or the adhesive in active agent layer 120. The selection of the removable release-liner 110 is dependent on the type of the adhesive in use, and is well known to a person skilled in the art. The releaseliner 110 is typically a polymer sheet or a paper coated with a polymer, which have rather weak adhesion toward the adhesive layer 180, therefore allowing itself being easily removed prior to use without damaging the adhesive layer 180.

In addition to or in lieu of the adhesive, the apparatus 500 may be fastened to the body surface with an adhesive tape, an elastic band, a band with a buckle (similar to a leather watch band), or a Velcro® band or the like.

In order to use the device 500, the removable release liner 110 is peeled off, and the pressure-sensitive adhesive 180, if present, and the active agent-containing layer 120 of the device 500 is affixed to the a barrier membrane (e.g., the skin) of the user. For the devices shown in FIGS. 1–3, it is affixed to the go skin directly if the active agent-containing layer 120 contains an adhesive, or it is affixed to the skin with additional adhesive bandage on their peripheral edges as an integral part of the device (not shown in the figures).

The target temperature range according to the present invention is between about 38° to about 50° C. (e.g., between about 40° C. to 42° C). The heating period in the present invention may vary dependent on the active agent being delivered and may range from a few minutes to longer than a day. In general, if the heating duration is short (e.g., less than 10 minutes), the operating temperature may be at the higher end of the above temperature range. However, if the heating period is longer, a lower operating temperature (e.g., less than about 43° C. )is used to avoid heat-related tissue injury.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. An multi-layer exothermic bandage, said bandage comprising:
   (a) an oxygen-impermeable layer;
   (b) a water-impermeable layer;
   (c) a heating element layer, said heating element layer comprising an oxidizable material, and where said heating element layer is between said oxygen-impermeable layer and said water-impermeable layer; and
   (d) an active agent layer, said active agent layer comprising an active agent;
   wherein said water-impermeable layer is between said heating element and said active agent layer.

2. A bandage of claim 1, wherein said bandage further comprises an adhesive where said liquid-impermeable layer is between said adhesive and said heating element layer.

3. A bandage of claim 2, wherein said adhesive is within said active agent layer.

4. A device of claim 1, wherein said device further comprises a removable liner where said active agent layer is between said liquid-impermeable layer and said removable liner.

5. A device of claim 1, wherein said heating element layer further comprises a salt, said salt selected from the group consisting of NaCl, KCl, $CaCl_2$, $FeCl_3$, $FeCl_2$, $MgCl_2$, $AlCl_3$, $Na_2SO_4$, $K_2SO_4$, $Fe(SO_4)_3$, $FeSO_4$, or $MgSO_4$.

6. A device of claim 1, wherein said oxidizable material comprises carbon and metal powder, said metal powder selected from the group consisting of iron, aluminum, magnesium, zinc, and a mixture thereof.

7. A device of claim 1, wherein said oxidizable material comprises carbon and an inorganic powder, said inorganic powder selected from the group consisting of ferrosoferric oxide, plumboblumbic oxide, trimanganese tetroxide, black copper oxide and manganese dioxide.

8. A device of claim 1, wherein said heating element layer further comprises a polymer.

9. A device of claim 1, wherein said heating element layer further comprises water.

10. A device of claim 1, wherein said device further comprises a heat-insulating layer where said oxygen-impermeable layer is between said heating element and said oxygen-impermeable layer.

11. A device of claim 1, wherein said exothermic reaction is between about 40° C. and 42° C.

12. A device of claim 1, wherein said active agent is for the treatment of acne.

13. A device of claim 1, wherein said device comprises at least one perforation where said perforation passes through said oxygen-impermeable layer, said water-impermeable layer, said heating element layer, and said active agent layer.

14. A method of topically delivering an active agent to a mammal, said method comprising attaching the bandage of claim 1 to a barrier membrane of said mammal.

15. A method of claim 14, wherein said mammal is a human.

16. A method of claim 15, wherein said device is attached to the skin of said human.

17. A method of claim 15, wherein said device is attached a mucosal layer of said human.

* * * * *